(12) United States Patent
Bertoncini et al.

(10) Patent No.: US 8,027,792 B2
(45) Date of Patent: Sep. 27, 2011

(54) METHOD FOR CARRYING OUT A QUANTITATIVE ANALYSIS OF A MIXTURE OF MOLECULAR COMPOUNDS BY TWO-DIMENSIONAL GAS CHROMATOGRAPHY

(75) Inventors: Fabrice Bertoncini, Lyons (FR); Benoît Celse, Genas (FR); Laurent Duval, Nanterre (FR)

(73) Assignee: Institut Francais du Petrole, Cedex (FR)

( * ) Notice: Subject to any disclaimer, the term of this patent is extended or adjusted under 35 U.S.C. 154(b) by 900 days.

(21) Appl. No.: 12/022,216

(22) Filed: Jan. 30, 2008

(65) Prior Publication Data

US 2008/0180447 A1 Jul. 31, 2008

(30) Foreign Application Priority Data

Jan. 30, 2007 (FR) ...................................... 07 00699

(51) Int. Cl.
*G01N 31/00* (2006.01)

(52) U.S. Cl. .............. 702/24; 702/28; 702/30; 73/23.36
(58) Field of Classification Search .............. 702/22–24, 702/27, 28, 30–32; 73/23.22, 23.23, 23.35, 73/23.36–23.39; 422/83, 89; 436/161
See application file for complete search history.

(56) References Cited

U.S. PATENT DOCUMENTS

| 5,196,039 A | 3/1993 | Phillips et al. |
| 2010/0050741 A1* | 3/2010 | Wang ........................... 73/23.39 |

OTHER PUBLICATIONS

Beens, Jan et al: "Quantitative Aspects of Comprehensive Two-Dimensional Gas Chromatography (GC×GC)" Journal of High Resolution Chromatography, vol. 21, Jan. 1998, pp. 47-54, XP002440106.
Vendeuvre, C., et al: "Characterisation of Middle-distitallates by Comprehensive Two-dimensional Gas Chromatography (GC×GC): A Powerful Alternative for Performing Various Standard Analysis of Middle-distillates" Journal of Chromatography A, Elsevier, Amsterdam, NL, vol. 1086, No. 1-2, Sep. 9, 2005, pp. 21-28, XP004995136.
Anonymous: "GC Image User's Guide: Pattern Recognition" [Online] Dec. 14, 2005, pp. 1-7, XP0024400107.
Reichenbach, S. E., et al: "Information Technologies for Comprehensive Two-dimensional Gas Chromatograpy", Chemometrics and Intelligent Laboratory Systems, Elsevier Science Publishers B.V. Amsterdam, NL, vol. 71, No. 2, May 28, 2004, pp. 107-120, XP004506974, ISSN: 0169-7439.

(Continued)

*Primary Examiner* — Manuel L Barbee
(74) *Attorney, Agent, or Firm* — Antonelli, Terry, Stout & Kraus, LLP.

(57) ABSTRACT

The Invention is a method for quantitative analysis of a mixture of molecular compounds by two-dimensional gas chromatography having application for quantitative analysis of products from the chemical or petroleum industry. A two-dimensional gas chromatography is carried out, during which a chromatographic signal is recorded. A chromatogram in two dimensions on which chromatographic peaks form spots is generated from the signal. These spots are defined by means of polygons. Then, for each polygon, chromatographic signal portions contained between two intersections of the polygon with columns of the chromatogram are extracted. Start and end times are defined for the chromatographic peaks present in these portions and the polygon is adjusted by shifting its intersection points according to the start and end times of the chromatographic peaks. Finally, molecular compound amounts are determined by calculating the surface area of the polygons thus adjusted.

35 Claims, 6 Drawing Sheets

OTHER PUBLICATIONS

Peters, Sonja et al: "Development of an Algorithm for Peak Detection in Comprehensive Two-dimensional Chromatography", Journal of Chromatography A, vol. 1156, 2007, pp. 14-24, XP002440108 Elsevier, Published On line Nov. 21, 2006.

Song, Qiang et al: "Digital Image Processing for a New Type of Chemical Separation System", Proceedings SPIE Conference on Applications of Digital Image Processing, Denver, Colorado, USA, Jul. 1999, vol. 3808, Oct. 1999, pp. 2-11, XP002440109 SPIE.

* cited by examiner

METHOD FOR CARRYING OUT A QUANTITATIVE ANALYSIS OF A MIXTURE OF MOLECULAR COMPOUNDS BY TWO-DIMENSIONAL GAS CHROMATOGRAPHY

BACKGROUND OF THE INVENTION

1. Field of the Invention

The present invention relates to two-dimensional gas chromatography analysis. In particular, the invention is a method for quantitative analysis of petroleum samples by two-dimensional gas chromatography.

2. Description of the Prior Art

Two-dimensional gas chromatography (2D GC) is a particularly efficient separation technique for performing detailed molecular analyses. This well-known technique is for example described in U.S. Pat. Nos. 5,135,549 and 5,196,039. These patents describe the principle of continuous coupling of two different separation columns in order to obtain two-dimensional chromatograms.

Two-dimensional gas chromatography is a separation technique wherein all the eluted compounds of a first column are successively subjected to a separation in a second column of different selectivity. The two columns are connected in series by means of a modulator that is the key element of the device. This interface samples the effluent of the first column in a form of chemical impulses and it transfers them to the second column. The time required for performing this operation, referred to as modulation period, generally requires a very fast (some seconds) second separation: the characteristics of the second column are selected in such a way that each impulse is separated during the modulation period. FIG. 1 diagrammatically shows the principle of 2D-GC.

The more affinity the compound has with the stationary phase, the more time it will need to leave each column. At the outlet of the second column, the compounds encounter a detector. This device measures various physical properties of the gaseous mixture in its form of an intensity as a function of time. This signal, referred to as chromatographic signal or "raw 1D" signal, comprises a set of peaks, characteristic of each constituent, whose shape depends on the intensity of the property measured. Each peak is called "elution peak" or "chromatographic peak". The maximum intensity corresponding to a peak is referred to as retention time. The signal thus recorded can be of different nature depending on the detector used. The detectors (TCD, FID, SCD, NCD, ...) are selected according to the application type by the person skilled in the art.

Some detectors allow detection of ppm (parts per million) of a component.

The elution peak from the first column is periodically sampled by the modulator. Each fraction is focused, then continuously injected into the second column. The detected chromatographic signal, the raw 1D signal, thus corresponds to a succession of separations (materialized by peaks on the signal) carried out in the second dimension. By combining these chromatograms with an offset, it is possible to reconstruct a signal in two dimensions: the beginning of each modulation cycle marks the retention time of a compound in the first dimension, whereas the maximum of each peak marks the retention time in the second dimension. An offset has to be introduced for the retention order in the second dimension to be correct. It allows shifting all the retention times on the ordinate axis by a constant value. This operation is useful to correctly represent the structure of a chromatogram wherein the absolute secondary retention time (that is on the y-axis) of a compound is greater than the modulation period, provided that the retention time difference between the less retained compound and the most retained compound is smaller than the modulation period (that is absence of separation overlap, or wrapping around).

The result can come in a form of a three-dimensional chromatogram, two of the axes representing the retention times on each of the separation dimensions, and the third axis indicating the intensity of the signal (3D in FIG. 1). The commonest representation is two-dimensional (2D chromatogram) wherein the two axes of the separation plane indicating the temporal coordinates. The chromatographic peaks (elution peaks) then form spots whose intensity is shown by a color gradation. This representation is close to a molecular image of the sample. In the example shown in FIG. 1, two solutes co-eluted after the first separation are separated during the second separation, provided that the nature of the stationary phases coating each column is suited thereto.

However, the results obtained from a two-dimensional gas chromatography (2D-GC) have to be coupled with complex data analysis methods.

As in conventional GC (gas chromatography), quantification of a solute in 2D-GC is carried out by calibrating the response of the detector by the measurement of the surface area of the elution peak. In the specific case of 2D-GC, the chromatogram is generally represented in a form of an iso-response surface that has to be integrated to obtain the volume of an elution peak proportional to the amount of solute introduced. As mentioned in the publication below, there are three known types of two-dimensional gas chromatography (2D-GC) quantitative analyses. All these methods are based on the definition of zones delimiting the spots representative of the elution peaks. These zones are referred to as "blobs" by specialists.

Van Mispelaar V. G. et al., 2005, *"Novel System for Classifying Chromatographic Applications, Exemplified by Comprehensive Two Dimensional Gas Chromatography and Multivariate Analysis"*, Journal of Chromatography A., 1071 (2005) pp. 229-237.

1—Determination of the Concentrations of a Certain Number of Predefined Compounds The compounds are identified by their retention times on the two axes (that is the maximum time of a zone). The surface area of the zone is converted to concentration by calibration. A clear return to the base line between two zones is assumed in this analysis. The base line corresponds to the signal recorded in the absence of compounds (that is in the presence of the mobile phase alone).

2—Determination of the Concentrations of Peak Groups

For some applications, the number of peaks is tens of thousands with strong co-elutions. It is then practically impossible to identify each peak individually. The goal is to group them together according to pseudo-components having common chemical or structural properties (same chemical type (structural homologs) with the same number of carbon atoms, the same number of double bonds, and the same number of aromatic rings, etc.).

3—Determination of the Similarities and Differences Between Several Analyses

The goal is to automatically determine the differences in terms of presence and concentration of compounds. Image processing and classification techniques are used. These techniques are used in particular for follow-up analyses or for sample screening, while disregarding the analytical details.

There are three types of operating methods for implementing this type of analysis.

Mode 1. The principle is as follows:

Definition of a generic mask of contour zones for each constituent (or blob) for an image type. Meta-data (name of the component, properties of the component) are possibly added.

Application of the mask to a new image.

Manual modification of the blobs to determine the exact position in the new image of each contour so as to take account of (i) the experimental uncertainties and of (ii) the variations linked with the concentration of the constituents.

This operating method is provided in the software GC Image® (Zoex, USA). This operating method is difficult to apply: in fact, the definition of the contour zones of each blob greatly depends on the user and on the way the individual peaks are defined from the complete image. The method is therefore neither very accurate nor very repeatable.

Mode 2. The principle is as follows:

Automatic determination of all the peaks of the image by image analysis

One-to-one association of a peak with a blob

Manual assignment of a chemical compound for each blob.

This operating method is described in the publication below. The peaks are determined directly in the image by means of a watershed type algorithm.

S. E. Reichenbach, V. Kottapalli, M. Ni, A. Visvanathan, 2005, *Computer Language for Identifying Chemicals with Comprehensive Two-Dimensional Gas Chromatography and Mass Spectrometry, Journal of Chromatography*, Vol. 1071, pp. 263-269.

This method is not suited to analysis of type 2 because the number of peaks is too large (several thousands). It is then impossible to assign a component to each peak. Furthermore, the implicit assumption of one-to-one relation between a blob and a peak is wrong: a blob often consists of several peaks.

Mode 3. The principle is as follows:

Automatic determination of all the peaks of the image

Identification of the peaks by rules. This operating method is described in the following publication:

M. Ni, S. E. Reichenbach, A. Visvanathan, J. TerMaat, E. B. Ledford, 2005, *Peak Pattern Variations Related to Comprehensive Two-Dimensional Gas Chromatography, Journal of Chromatography*, Vol. 1086, pp. 165-170. Setting up the rules is complicated.

Mode 4. The principle is as follows:

Automatic determination of all the peaks of the raw 1D signal (SB) corresponding to the image by conventional integration (1D GC techniques).

Definition of zones (blobs) in the image by the user.

The final surface area of the blob corresponds to the sum of the surface areas of the peaks of the raw 1D signal (SB) belonging to the blob.

This operating method is provided by the software Hyper-Chrom® (Thermo, USA).

Daniela Cavagnino, Paolo Magni, Giacinto Zilioli, Sorin Trestianu, 2003, *Comprehensive Two-Dimensional Gas Chromatography Using Large Sample Volume Injection for the Determination of Polynuclear Aromatic Hydrocarbons in Complex Matrices, Journal of Chromatography A*, 1019 (2003) 211-220.

This method however involves the following drawbacks:

It is not possible to define a mask predefining several blobs to be applied for each new analysis (pattern). For each new analysis, the user has to define a new mask, which is costly in analysis time and operator-dependent.

A blob is necessarily a predefined quadrilateral that can be deformed thereafter. Some blobs therefore cannot be correctly positioned for correctly trimming each elution peak.

Now, according to type 2, it must be possible to define zones corresponding to several hundred peaks whose contour can be very tortuous.

In case of strong co-elutions, it can be very difficult to precisely define the elution peaks in the secondary chromatogram corresponding to the second separation. In this case, the proposed integration is generally erroneous because the zone to be integrated from the blob is not well defined. There is no a posteriori control in case of absence of detection of a peak.

The user cannot really visualize the limits of each blob.

Mode 5. The principle is as follows:

Definition of a mask of zones (blob) in the image

Automatic determination of all the peaks of the image

Assignment of the previously defined peaks to the blobs via statistical analyses.

This operating method is described in the following publication:

M. Ni, S. E. Reichenbach 2005, *Using Edge Pattern Matching for Automatic Chemical Identification in GC 2D, Automatic Target Recognition XIV*. Edited by Sadjadi, Firooz A. Proceedings of the SPIE, Volume 5426, pp. 155-163 (2004).

The adjustment between the images is performed peak by peak. The authors reduce the data by working only on the peak maximum. However, they implicitly assume a one-to-one relation between a peak and a blob (and therefore a chemical component). This is not the case in practice. Furthermore, the method provided greatly depends on the chemical composition of the product. Since a blob can contain several peaks whose concentration ratio can vary, the maximum of a blob can be very variable.

In short, two-dimensional gas chromatography is a particularly efficient technique that is used in the industry to carry out quantitative analyses of samples such as petroleum samples for example. This technique however involves complex analysis methods. Current analysis methods are not entirely satisfactory:

the definition of polygons defining the spots in the image is sometimes difficult because the number of peaks is very large. These zones can also involve several peaks, identification of the zones (blobs): associating a chemical compound with a zone is delicate. The larger the number of carbon atoms, the larger the number of isomers. It is then delicate to associate a component with a peak.

Furthermore, these methods of analyzing two-dimensional gas chromatography (2D GC) results are manual and they therefore have two major drawbacks: they require much time and their results depend on the interpreter. Such analyses are therefore difficult to use in practice because of their inaccuracies. Because the number of polygons is general above 150, automated methods have to be applied.

SUMMARY OF THE INVENTION

The present invention provides a new methodology for analyzing two-dimensional gas chromatography results, allowing overcoming the aforementioned problems, and notably to provide an analysis method allowing on the one hand automatic adjustment of the shape of the polygons surrounding the zones (blobs) and, on the other hand, allowing using polygon masks for other analyses by automatically recalibrating the polygons in the new image (2D chromatogram).

The invention relates to a method for quantitative analysis of a mixture of molecular compounds by two-dimensional gas chromatography, comprising:

recording a chromatographic signal (SB) comprising chromatographic peaks;

generating a chromatogram (CHR) in two dimensions wherein each column corresponds to a portion of the chromatographic signal and the chromatographic peaks form spots in the chromatogram; and defining the spots by use of polygons.

The method comprises the following for at least one polygon:

identifying portions of the chromatographic signal contained between two intersections of the polygon with columns of the chromatogram;

determining start times, end times and maximums for chromatographic peaks present in the portions;

adjusting the polygon by shifting the intersection points according to the start times, the end times and maximums of the chromatographic peaks; and determining an amount of at least one molecular compound by calculating the surface area of the adjusted polygon.

According to the method, the polygon can be adjusted by carrying out the following for each intersection point between the polygon and a column of the chromatogram:

if the intersection point is contained between the start and the maximum of a chromatographic peak, the point is shifted towards the peak start point;

if the intersection point is contained between the maximum and the end of a chromatographic peak, the point is shifted towards the peak end time; and if the intersection point is not contained between a start time and an end time of a chromatographic peak, the point is shifted vertically along a column towards the closest peak, as long as the point does not merge with the boundary of the polygon, or with the boundary of the chromatogram, or with a chromatographic peak start or end.

The polygons can also be adjusted starting from a first point of the polygon and, as long as the last point is not processed, by removing a point from the middle if a current point is aligned with the next two points, and going two points back, or going to the next point. It is also possible to calculate the final position of a polygon vertex by a linear interpolation with respect to the neighboring vertices.

According to the invention, the spots can be defined by constructing polygons manually, or by means of a polygon mask suited to the two-dimensional gas chromatography used by replacing each vertex forming the polygon in the closest column of the chromatogram.

The start times, the end times and the chromatographic peak maximums can be determined from the first, second and third derivatives of the portions of the chromatographic signal. The derivatives can be calculated by Savitzky-Golay filtering.

BRIEF DESCRIPTION OF THE DRAWINGS

Other features and advantages of the method according to the invention will be clear from reading the description hereafter of non limitative embodiment examples, with reference to the accompanying figures wherein.

DETAILED DESCRIPTION

The method according to the invention allows carrying out quantitative analyses of mixtures of molecular compounds, such as petroleum products, by analyzing chromatograms obtained by two-dimensional gas chromatography.

After carrying out a two-dimensional gas chromatography (2D-GC) on a sample whose molecular composition is to be determined, the method mainly comprises four parts (FIG. 6):

1—Constructing a chromatogram in two dimensions (CHR) from the two-dimensional gas chromatography (2D-GC);

2—Defining the spots of the chromatogram by polygons (POL);

3—Adjusting the polygons to the spots identified in the chromatogram (ADJ); and

4—Determining the molecular composition of the sample by analyzing the polygons (COMP).

1—Construction of a Chromatogram in Two Dimensions

The image to which the method is applied is a chromatogram in two dimensions. Such a chromatogram is characterized by the following elements:

the modulation period (MC2): time required for sampling the effluent of the first column in the form of chemical impulses and for transferring them to the second column;

temporal coordinate of the first point taken into account (TS: Time Start). This point is selected by the user because the signal starts are sometimes unexploitable and second column offset (OC2).

Figure 1:
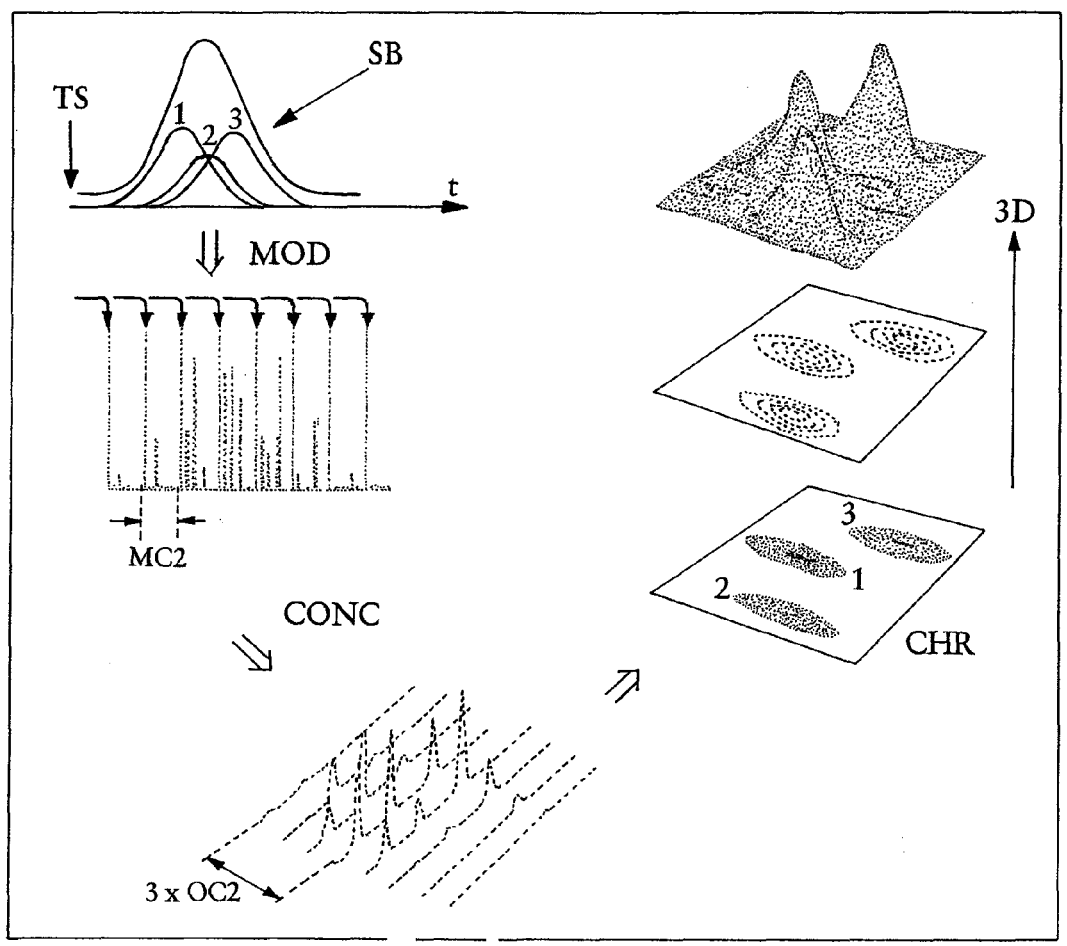
FIG. 1 illustrates the construction principle of a 2D-GC chromatogram.
Figure 2:
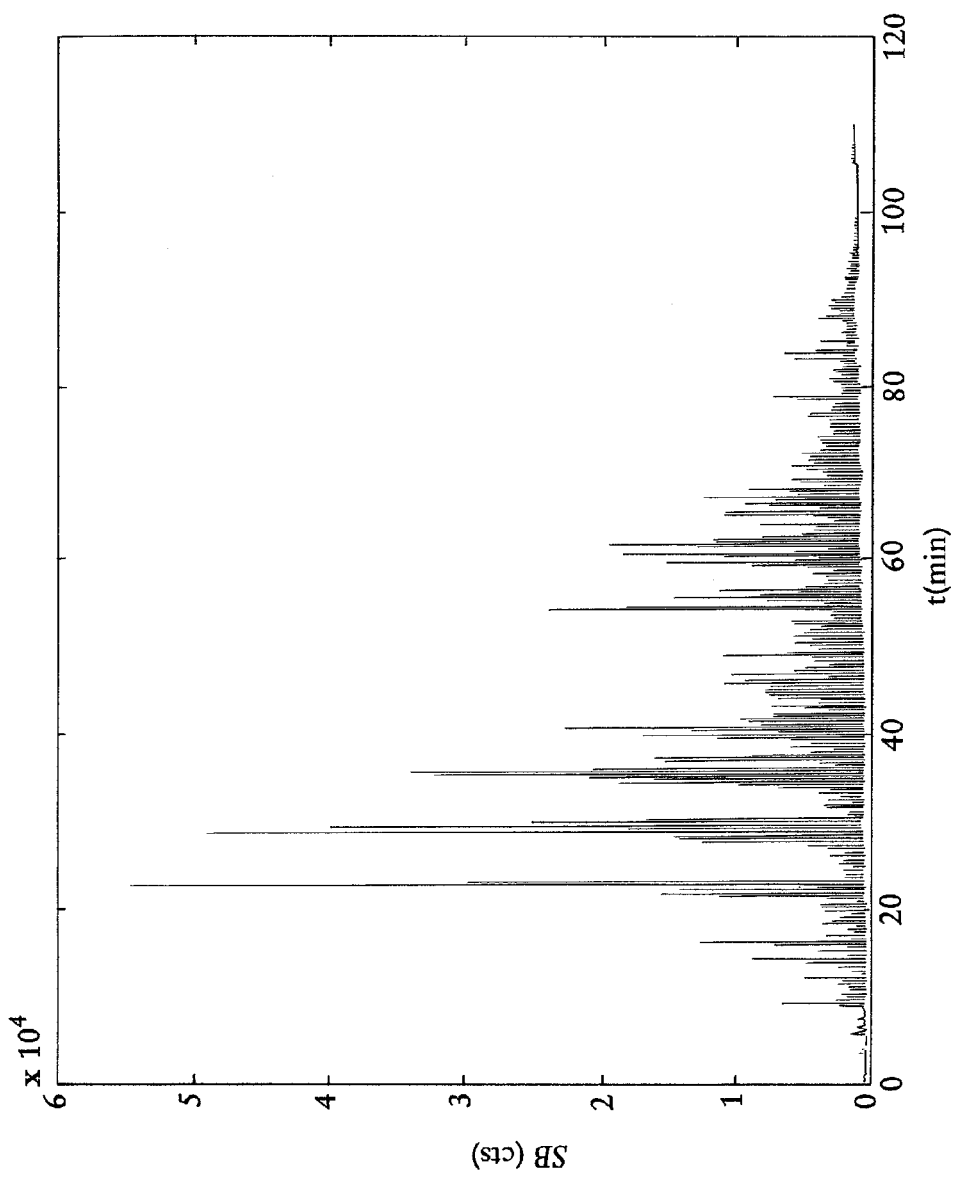
FIG. 2 illustrates a raw 1D signal (SB) recorded as a function of time (t) by the detector at the outlet of the second column.

This chromatogram is constructed as follows (FIG. 1):

during the two-dimensional gas chromatography, a raw 1D signal (chromatographic signal) corresponding to the signal recorded by the detector at the second column outlet as a function of time (t) is recorded. Such a raw 1D signal (SB) is shown as a function of time (t) in FIG. 2. It has a set of points P(t);

the points of this chromatographic signal (SB) having a temporal coordinate below TS+OC2 are removed from the signal;

the signal is divided into successive pieces of length MC2, which corresponds to the modulation (MOD), these pieces are concatenated (CONC) vertically side by side so as to form a 2D image referred to as 2D chromatogram (CHR). The offset between the columns is OC2.

Figure 3:
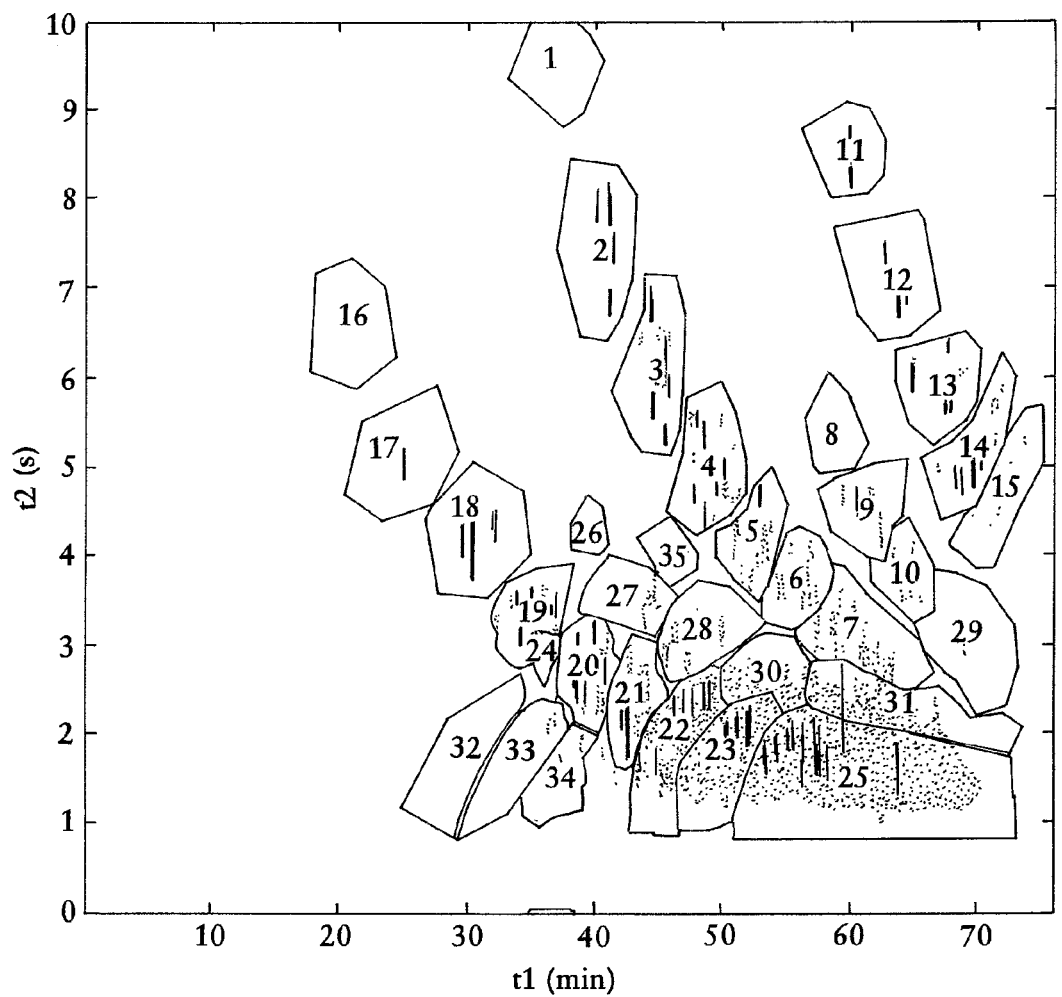
FIG. 3 shows a 2D chromatogram obtained for the separation of nitrogen-containing compounds contained in a middle distillate sample.

This 2D chromatogram is the commonest representation. It therefore has a set of slices (of width equal to the modulation period MC2) of raw data concatenated side by side. FIG. 3 shows a 2D chromatogram obtained for the separation of nitrogen-containing compounds contained in a middle distillate sample. The two axes of the separation plane indicate the separation temporal coordinates for the first column as the abscissa and for the second column as the ordinate. Chromatographic peaks then form spots whose intensity is shown by a colour gradation. This representation is close to a molecular image of the sample.

Carrying out these operations amounts to applying the following formulas at each point P(t) of the raw 1D signal (SB) having a temporal coordinate greater than TS+OC2:

$$x = MC2 * \mathrm{floor}((t-TS-OC2)/MC2) + TS + OC2 \quad (1)$$

$$y = \mathrm{mod}((t-TS-OC2); MC2) \quad (2)$$

with:
- t: temporal position of point P(t) on the raw 1D signal;
- x, y: the spatial coordinates in the 2D chromatogram of point P(t);
- floor: function that returns the greatest integer that is not greater than the argument; and
- mod: function that returns the remainder of a division.

It can be noted that relations (1) and (2) expressed above, which allow calculation of the spatial coordinates (x, y) of a point P(t) from its temporal coordinates, are reversible: t=x+y. This relation connecting the absolute time (t) and the coordinates (x, y) of a point in the image is respected for any point appearing in this image (2D chromatogram), whether obtained from the raw 1D signal (SB) or from the definition of a polygon.

2—Definition of the Spots by Polygons in the Chromatogram

The constructed 2D chromatogram exhibits spots whose intensity is expressed by a color gradation and which represent the chromatographic peaks. The surface area of these spots is proportional to the amount of a specific molecular compound. A spot is a zone of the 2D chromatogram comprising at least one elution peak. These spots are referred in the technology as "blobs". These spots are small spaces of different colors (color of the peaks) standing out against a background of another color (base line color). These zones therefore have to be first defined. This definition forms a polygon, that is a closed geometrical figure limited by segments of a line (sides), each one having a common end (vertex) with the previous and the next one.

Two options can be considered. Either the polygons are created manually by a person who interprets the 2D image, or a polygon mask, that is a set of previously determined polygons, is applied. It can be a mask resulting from a prior analysis of a similar solute for example.

In the second case, the mask has to be suited to the study in progress. The above paragraph has shown how the 2D image (the 2D chromatogram) has juxtapositions of segments of the raw 1D signal (SB) drawn vertically. The relation t=x+y that connects the points of the image to those of the raw 1D signal (SB) is valid only for the points at the center of the columns. It can therefore not be applied directly. A horizontal recalibration is necessary. It replaces each polygon vertex (12, 17) with the user's mouse on the closest column:

$$x' = \text{round}((x-OC2-TS)/MC2)*MC2+OC2+TS$$

with round: function returning the integer that is the closest to the number turned into the argument.

With a fixed offset of the second column (OC2), temporal coordinate of the first point taken into account (TS) and the modulation period (MC2), a bijection t=x+y can be defined. It associates at any time a set of coordinates in the image. The polygons are thus stored in the form as follows:
- {tk}: temporal coordinates on the raw 1D signal (SB) of the k vertices of the polygon;
- OC2: second column offset upon creation of the polygon;
- TS: value of the temporal coordinate of the first point taken into account upon creation of the polygon; and
- MC2: modulation period upon creation of the polygon.

Storage of the modulation period allows determination of whether a polygon is coherent with the acquisition parameters of an analysis (same period). Storage of the second column offset and of the TS allows having at least one configuration wherein the entire polygon is visible in the image. This storage mode allows readily re-applying a polygon mask to a new analysis even if the offset used is different. The polygon vertex addition, suppression, modification functionalities can then be readily implemented: the spatial positions are automatically converted to temporal positions. This data structure then allows:
- having a bijective relation between the image and the raw 1D signal (SB);
- being independent of the offset selected by the user with a polygon mask defined with a certain offset can be applied to a new analysis even if it has a different offset; and
- using the times corresponding to the integration on a raw 1D signal (SB) to recalibrate the points in the 2D image.

3—Adjustment of the Polygons to Spots Identified in the Chromatogram

The data structure described above allows applying a polygon mask to a new analysis (independently of the offset). The goal is then to recalibrate the polygons on a new analysis, that is to calibrate them on elution peak start and end times on the 1D signals corresponding to the intersection between the columns of the image and the polygon. Adjustment of the polygons is divided up into three distinct stages:
- determination of 1D signals (pieces of the raw 1D signal (SB)) corresponding to the intersection between a polygon and the columns of the image;
- determination of elution peaks on this 1D signal; and
- adjustment of a polygon on the previously calculated peak start and end times.

Figure 6:
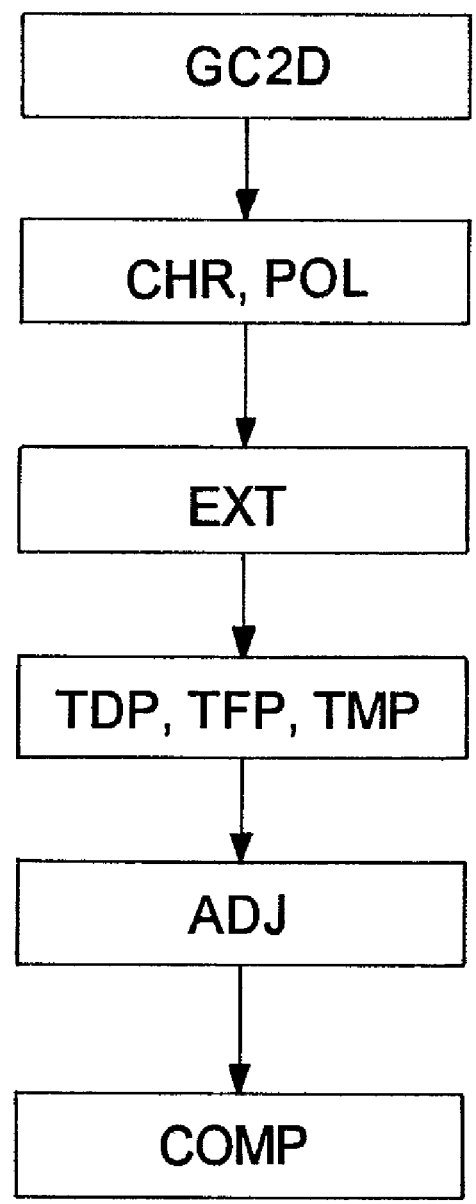
FIG. 6 illustrates the stages of the method according to the invention.

3.1—Determination of the Chromatographic Signal (SB) Portions to be Processed (EXT—FIG. 6)

The initial operation is the determination of all of the points in the 2D chromatogram defining the contour of a zone that is a polygon. Extraction of 1D signal portions is carried out by following the stages below, for each polygon segment, in the direction of storage of the polygon vertices:
- let A and B be the two ends of a segment, tA and tB their temporal coordinates;
- let n=(floor((tB−tA)/MC2)−1) be the number of columns of the image crossed by segment AB, excluding the ends; and
- knowing the number of columns, the temporal coordinates of the polygon vertices: tk=tA+k*(tB−tA)/(n+1), with k ranging from 1 to n, are calculated by intersection between the side of the polygon and each column.

Particular Cases

The processings applied to the 1D signal require an alternation of pairs denoted by [$T_{IN}$; $T_{OUT}$] for the points obtained, once sorted out, which define the signal portions positioned within the polygon. A certain number of particular configurations have to be sought.

When the polygon comprises a laterally oriented pointed outgrowth, the vertex has to be duplicated ($T_{IN}=T_{OUT}$) so that the possibly superposed signal point is taken into account in the calculations;

When the polygon comprises a laterally oriented pointed hole, the vertex has to be truncated so as not to count the point possibly superposed with the vertex twice; and When the polygon comprises vertical segments surrounded by two segments going in different directions, the end of the segment that defines the concave point has to be suppressed in order to prevent the $T_{IN}$ $T_{OUT}$ alternation from being broken.

At the end of this stage, the chromatographic signal (SB) portions contained between two polygon intersections with chromatogram columns are extracted.

3.2—Determination of the Peaks on the 1D Signal Portions (TDP, TFP, TMP—FIG. 6)

The previous paragraph has allowed determination of the start and end times of each column of the image belonging to the polygon which is considered to define chromatographic signal portions. This paragraph is more specific about the method developed for determining on the obtained portions the start times (TDP), the maximum times (TMP) and the end times (TFP) of each peak.

Determining peaks on a 1D signal is generally carried out via derivative calculations: first and second derivatives for weak co-elutions, and first, second and third derivatives for strong co-elutions. The following publication lists the various methods used:

G. Vivo-Truyols a, J. R. Torres-Lapasi, A. M. van Nederkassel, Y. Vander Heyden, D. L. Massart, 2005, *Automatic Program for Peak Detection and Deconvolution of Multi-Overlapped Chromatograhic Signals, Journal of Chromatography A,* 1096 (2005) 133-145.

However, the above authors show that the use of the first derivative is not sufficient in the case of strong co-elutions (that is the two peaks are very close, it is very difficult to visually detect the presence of the two peaks): there is no return to zero of the first derivative. Thus, according to the invention, the peak detection method comprises the following parts, for each 1D signal portion obtained:

1—Calculation of the first, second (and possibly third) derivatives of the 1D signal portions.
2—Calculation of the processing thresholds. They are determined by trial and error. The values are fixed for each product type.
3—Detection of the Peaks on the Portion.
  For a Weak Co-Elution:
    the value of the first derivative is zero at P(t), negative before and positive after,
    the difference of the values of the first derivative between point P(t) and the next point is greater than threshold seuil3rd,
    the value of the second derivative at this point P(t) is negative and of amplitude greater than threshold seuil2nd,
    the value of the signal at this point P(t) is greater than threshold ampThreshold.
  For a strong co-elution, the first derivative is replaced by the third derivative:
    the value of the third derivative is zero at P(t), negative before and positive after;
    the difference of the values of the third derivative between point P(t) and the next point is greater than threshold seuil3rd;
    the value of the second derivative at this point P(t) is negative and of amplitude greater than threshold seuil2nd; and
    the value of the signal at this point P(t) is greater than threshold ampThreshold.

Calculation of the derivatives can be performed using preferably the Savitzky-Golay filtering method, but other robust filtering methods can be used. One such method is for example described in:

Savitzky A., Golay M. J. E.," *"Smoothing and Differentiation of Data by Simplified Least Squares Procedures"*, Anal. Chem., vol. 36, pp. 1627-1639, 1964.

If all these conditions are met at point P(t), an elution peak is recorded at this point or, more exactly, a chromatographic peak maximum is recorded at point P(t). Prior to detecting a new peak, a test is added to check that the second derivative recedes sufficiently from the "close to zero" zone. This zone is defined by the value of a threshold, seuilPeakProcheZero3rd.

4—Checking
  Seeking the start and end of each peak.
  For a weak co-elution, and for each peak:
    Determination of a sign variation of the first derivative. This corresponds to the first zero crossing.
    As long as the absolute value of the first derivative is below threshold seuilStartStopProcheZero3rd, no new zero crossing is sought.

Seeking a new zero crossing of the first derivative.
For a strong co-elution, the algorithm is identical but the third derivative is used.

A posteriori control:
If there is a peak between the current peak and the first zero crossing, then peak Stop (respectively Start) takes the value of the current peak.
If there is a peak between the current peak and the second zero crossing, then peak Stop (respectively Start) takes the value of the first zero crossing.
Otherwise, peak Stop (respectively Start) takes the value of the second zero crossing.

5—Refinement of the Results Obtained
Improvement of the first peak Start. Since the first peak Start has no neighbor with the previous one, it can be displaced to the start of the signal (processing is performed on a column) until the height of the signal does not exceed value ampThreshold. This allows taking account of more values for the first peak.

Possible gathering of peaks Start and Stop and of the neighboring peaks. When two peaks are neighboring peaks, the best solution can be to gather peak Stop of the previous neighbor and peak Start of the next neighbor. Prior to carrying out this gathering, the next test is performed on the minimum between the two points to be gathered. If this value is greater than ampThreshold, the two peaks are gathered at this point. Otherwise, they are not modified.

Improvement of the last peak Stop. Since the last peak Stop has no neighbor with the next one, it can be displaced to the end of the signal until the height of the signal no longer exceeds value ampThreshold. This allows taking account of more values for the last peak.

6—A Posteriori Analysis by Removing the Peaks that do not Meet the Following Critera:
  peak height smaller than a threshold fixed by the user;
  peak width smaller than a threshold fixed by the user; and
  peak surface area smaller than a threshold fixed by the user.

The following processing thresholds are thus used (fixed by trial and error for each product type). Values are given by way of non limitative example:

| | |
|---|---|
| seuil2nd | 5 |
| ampThreshold | 200 |
| seuil3rd | 2 |
| seuilPeakProcheZero3rd | 5 |
| seuilStartStopProcheZero3rd | 1 |

Thus, at the end of this part, the start times (peak Start), the maximum times (P(t)) and the end times (peak Stop) of each chromatographic peak present on the signal portions are known.

3.3—Adjustment of a Polygon on the Start and End Times of the Peaks

The above method has allowed determination of the start and end times of each peak on each column of the image. These times are thereafter used to automatically adjust the polygons. The bijective relation between the spatial coordinates and their temporal coordinates is used. The method follows the following:

For each intersection point between the polygon and a column of the image:
  If the point is on no peak (that is it is not contained between a peak Start and a peak Stop): as long as the point is not equal to the boundary of the polygon, or to the boundary of the image, or to a peak start or end, the point is shifted vertically towards the closest peak (start or end time of a peak).

If the point is contained between a peak start and maximum: the point is shifted towards the start of the peak.

If the point is contained between a peak maximum and a peak end, the point is shifted towards the end of the peak.

In some cases, two vertices that were vertically distant from one another become distant by a distance that is less than or equal to a pixel. They then merge. The following vertices are then suppressed:

the vertices grouped on the horizontal ends of the polygon; and the vertices whose horizontal neighbors are aligned with itself (therefore useless for memory storage of the contour).

This algorithm guarantees joints between the polygons. No part of the signal is therefore lost.

According to an embodiment, an additional stage of polygon simplification is added. In fact, the previous operations can produce polygons with some edges containing more than one point. It is therefore useful to be able to simplify them, if only to allow easier handling when modifications are requested by means of the mouse. The following method is used. Starting from the first point of the contour, and as long as the last one is not processed:

If the current point is aligned with the next two, then
Remove the point from the middle,
go two points back,
Otherwise, go to the next point.

A posteriori analysis of the contour: if the variation of the point is too great (in relation to the length of the portion), the final position of the point is calculated as the linear interpolation in relation to its neighbors. The final contour is thus obtained.

4—Determination of the Molecular Composition of the Sample

The spots of the 2D chromatogram represent a set of chromatographic peaks. The surface area of these spots is proportional to the amount of a specific molecular compound.

If all the temporal coordinates of the intersections of the polygon defining the polygon with the columns of the image are known and have been reprocessed according to the principles mentioned in the above paragraph, then the surface areas can be calculated simply with the following algorithm:

Sorting the temporal coordinates in increasing order (the slices will be defined for any k by [t2k−1 t2k]);

Adding double points on the crossing line of the edge of the image;

Adding up the values of the signal on the slices per column, and their cumulative sums.

The processings are carried out for each polygon only if the current modulation period is identical to the period stored in the polygon. The surface area calculations are all carried out with an offset calculated in such a way that the polygon is at the center of the image. This allows obtaining, for each analysis, result files independent of the second column offset. Only the geographical coordinates of the maximum of each polygon present in the result file then depend on the second column offset.

According to an embodiment, the polygons can be displayed. To assign a mask to a new analysis, it is essential to take account of the fact that the offset can be different. Furthermore, whatever the polygon being considered, there is a value for the second column offset that will shift it sufficiently towards the top or the bottom of the image so that it eventually crosses the edge, thus becoming partly invisible.

For the polygon to be completely visible, three successive stages are necessary:

Calculation of the coordinates of the polygon vertices in initial configuration (second column offset, TS and creation modulation period):

$$[x0,y0]=f(t,OC2,TS,MC2)$$

Shift to the current second column offset:

$$[x1,y1]=[x0,y0]+[OC2-OC20-OC2+OC20]$$

calculation and display of the polygons positioned "above" and "below" through shifting:

$$[x2,y2]=[x1,y1]+[MC2-MC2]$$

$$[x3,y3]=[x1,y1]+[-MC2MC2]$$

The three obtained polygons, all points of which meet t=x+y, are drawn. Thus, either the central polygon is totally visible, or it extends beyond the edge of the image, and one of the polygons "above" or "below" appears, representing the part extending beyond the image, and it re-appears on the other edge of the image.

Results Obtained

Figure 4A:
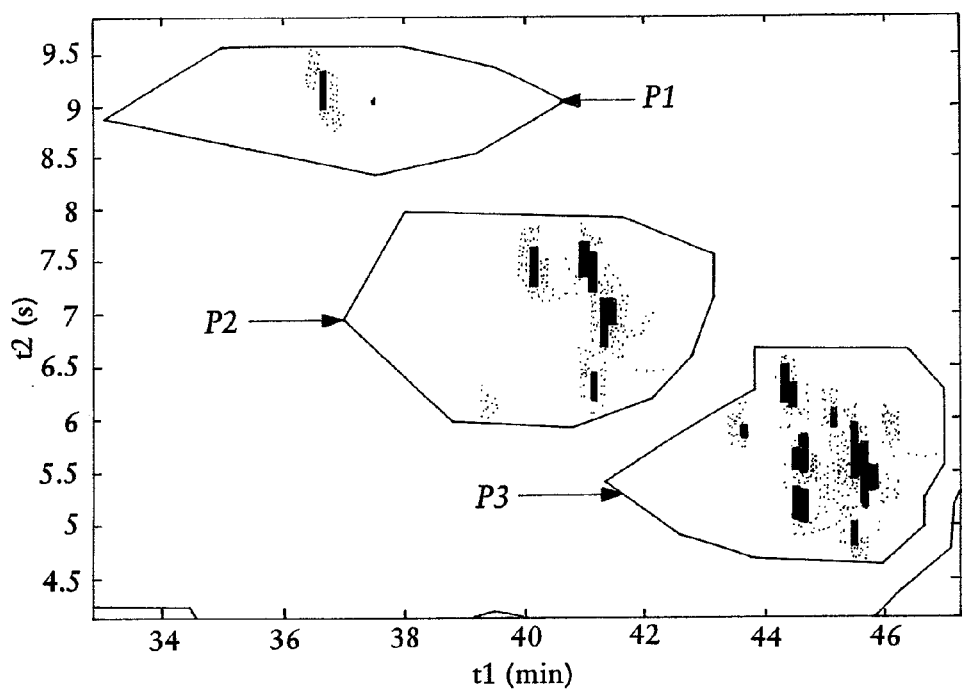
FIGS. 4A and 4B show three polygons (P1, P2 and P3) before (FIG. 4A) and after (FIG. 4B) tightening of the polygons on the chromatographic peaks.
Figure 4B:
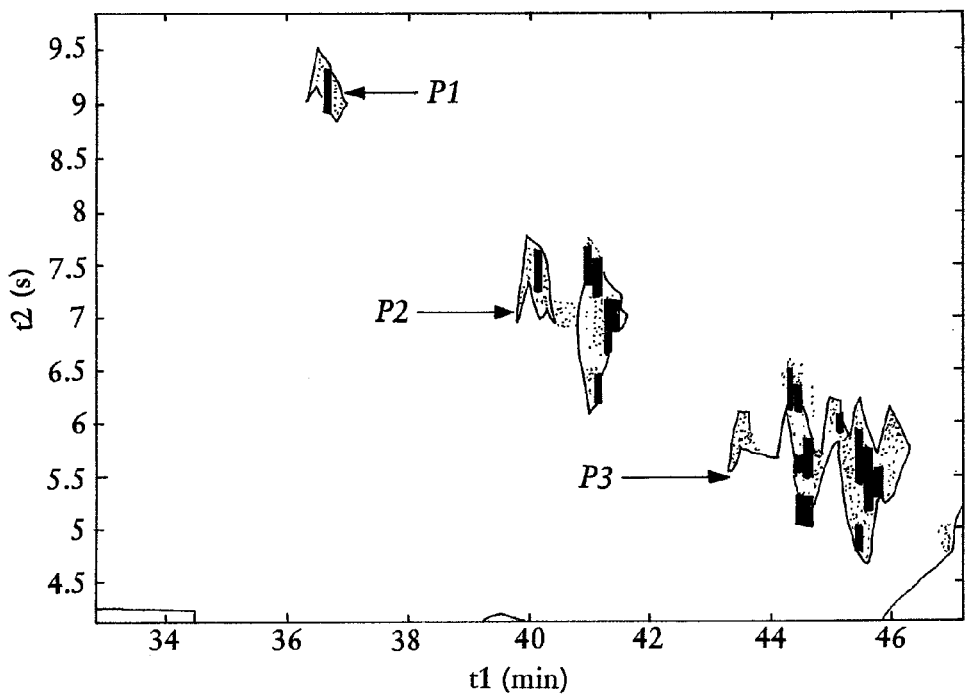
Figure 5A:
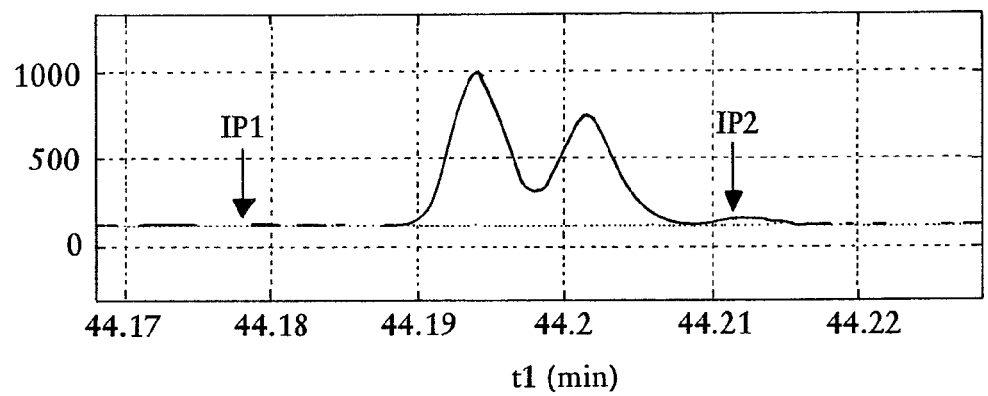
FIGS. 5A and 5B show a polygon before (FIG. 5A) and after (FIG. 5B) tightening on a chromatographic peak.
Figure 5B:
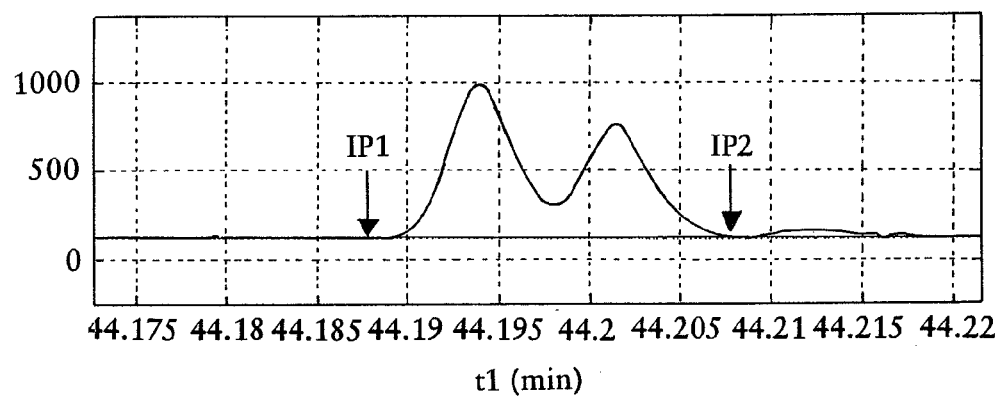

FIGS. 4A and 4B show three polygons (P1, P2 and P3) before (FIG. 4A) and after (FIG. 4B) tightening. The abscissa axis represents the separation time according to the first column (t1) and the ordinate axis represents the separation time according to the second column (t2). The lower and upper boundaries of the polygons correspond to peak starts and ends, as illustrated by FIG. 5A (before tightening) and 5B (after tightening) for polygon P2. The intersections of the polygon with the 1D signal are denoted by IP1 and IP2.

Tables 1 and 2 show the result of a repeatability study. The same sample is analyzed five times. The dispersion error is calculated by means of a Student test for an error level of 99%. The error is 25.6%. After tightening, the error is 16.2%. This corresponds to a notable repeatability improvement.

TABLE 1

Five manual analyses by 2D-GC of the same sample

| Blob numero | 20802 Sans | 20802_2 Sans | 020802_3 Sans | 020802_4 Sans | 020802_5 Sans | Moyenne Sans | Ecart Type | Intervalle de condiance a 99% | Ecart relatif Sans | Erreur de disp |
|---|---|---|---|---|---|---|---|---|---|---|
| 1 | 693.6132 | 677.422 | 638.9863 | 688.7529 | 600.0112 | 660 | 39.69 | 153 | 23.2 | 24.24167333 |
| 2 | 2632.8263 | 2760.8976 | 2554.0544 | 2795.0653 | 2618.5905 | 2672 | 101.67 | 391 | 14.6 | 15.33230536 |
| 3 | 4430.6724 | 4520.2499 | 4552.3978 | 4488.6817 | 4458.3786 | 4490 | 48.30 | 186 | 4.1 | 4.334714466 |
| 4 | 4371.3873 | 4409.2807 | 4560.4943 | 4193.0855 | 4269.2032 | 4361 | 140.41 | 541 | 12.4 | 12.97608431 |
| 5 | 2952.2289 | 3253.7824 | 2956.6574 | 3302.1977 | 3148.9983 | 3123 | 163.34 | 629 | 20.1 | 21.07977468 |
| 6 | 3236.0866 | 3237.5037 | 3378.3946 | 3368.8354 | 3606.3818 | 3365 | 151.11 | 582 | 17.3 | 18.09444814 |
| 8 | 1259.66 | 1218.1999 | 1210.8659 | 1190.1887 | 1113.1557 | 1198 | 53.93 | 208 | 17.3 | 18.13581695 |
| 9 | 2533.5911 | 2316.7573 | 2638.2751 | 2490.2113 | 2527.4731 | 2501 | 116.91 | 450 | 18.0 | 18.83588558 |

TABLE 1-continued

Five manual analyses by 2D-GC of the same sample

| Blob numero | 20802 Sans | 20802_2 Sans | 020802_3 Sans | 020802_4 Sans | 020802_5 Sans | Moyenne Sans | Ecart Type | Intervalle de condiance a 99% | Ecart relatif Sans | Erreur de disp |
|---|---|---|---|---|---|---|---|---|---|---|
| 10 | 2334.2034 | 2163.4456 | 2052.7626 | 2131.5606 | 2116.0108 | 2160 | 105.60 | 407 | 18.8 | 19.70505252 |
| 11 | 1453.451 | 1346.0544 | 1456.5842 | 1585.1523 | 1333.2416 | 1435 | 102.00 | 393 | 27.4 | 28.64807037 |
| 12 | 4746.8259 | 4600.3953 | 4634.1487 | 4659.3319 | 4550.3252 | 4638 | 73.17 | 282 | 6.1 | 6.357278762 |
| 13 | 5895.684 | 5897.3614 | 5970.0231 | 5948.8879 | 5891.6733 | 5921 | 36.20 | 139 | 2.4 | 2.463659877 |
| 14 | 4046.6803 | 4007.7299 | 4108.1151 | 4020.697 | 3974.0226 | 4031 | 50.21 | 193 | 4.8 | 5.019568544 |
| 16 | 405.6626 | 159.8395 | 209.1948 | 199.3375 | 216.3829 | 238 | 96.19 | 370 | 155.6 | 162.8226345 |
| 17 | 792.702 | 643.9954 | 707.9638 | 684.1475 | 542.2587 | 674 | 91.65 | 353 | 52.3 | 54.78521606 |
| 18 | 6014.4004 | 5859.8967 | 5851.3828 | 5854.5308 | 5834.8535 | 5883 | 74.04 | 285 | 4.8 | 5.071954037 |
| 19 | 9649.6001 | 9488.3745 | 9778.6676 | 9660.4628 | 9715.5641 | 9659 | 108.08 | 416 | 4.3 | 4.509474891 |
| 20 | 8913.5894 | 9024.296 | 8845.8939 | 9198.3286 | 8773.009 | 8951 | 166.34 | 640 | 7.2 | 7.488934271 |
| 24 | 370.4966 | 340.469 | 345.5483 | 315.5919 | 387.1903 | 352 | 27.75 | 107 | 30.4 | 31.78470349 |
| 26 | 297.7412 | 338.888 | 295.6542 | 299.1189 | 280.7397 | 302 | 21.67 | 83 | 27.6 | 28.87751123 |
| 27 | 1234.7348 | 1411.9928 | 1217.4489 | 1235.1751 | 1287.7685 | 1277 | 79.72 | 307 | 24.0 | 25.14946643 |
| 28 | 2886.1509 | 2869.4489 | 2862.6869 | 2814.2043 | 2829.2772 | 2852 | 29.70 | 114 | 4.0 | 4.196702337 |
| 32 | 911.9924 | 782.2021 | 920.9414 | 701.143 | 802.7238 | 824 | 92.78 | 357 | 43.4 | 45.38838304 |
| 34 | 1738.799 | 1705.1357 | 2313.468 | 2160.7415 | 1896.4163 | 1963 | 266.05 | 1024 | 52.2 | 54.62126328 |
| 35 | 310.281 | 277.8327 | 285.0977 | 313.8031 | 294.9582 | 296 | 15.57 | 60 | 20.2 | 21.17466407 |
| Somme | 74113.0608 | 73311.4514 | 74345.7078 | 74299.2332 | 73068.6081 | 2953.1 | 90.1 | 346.9 | 24.5 | 25.6 |

TABLE 2

Five manual analyses, then tightening by 2D-GC of the same sample

| | | | | | | | | | | |
|---|---|---|---|---|---|---|---|---|---|---|
| 1 | 327.0229 | 327.0229 | 327.0229 | 327.0229 | 327.0229 | 327 | 0.00 | 0 | 0.0 | 6.64817E−06 |
| 2 | 2049.1434 | 2049.1434 | 2049.1434 | 2049.1434 | 2049.1434 | 2049 | 0.00 | 0 | 0.0 | 0 |
| 3 | 3907.1145 | 3950.93 | 3951.0624 | 3857.1669 | 3907.1145 | 3915 | 38.92 | 150 | 3.8 | 4.006953873 |
| 4 | 3814.2792 | 3680.8984 | 3814.6387 | 3552.5253 | 3677.254 | 3708 | 110.14 | 424 | 11.4 | 11.97021108 |
| 5 | 2462.2322 | 2498.7872 | 2390.9256 | 2636.7412 | 2502.0068 | 2498 | 89.46 | 344 | 13.8 | 14.43115513 |
| 6 | 2776.5712 | 2707.5659 | 2870.9512 | 2798.4047 | 2994.0766 | 2830 | 108.90 | 419 | 14.8 | 15.51084172 |
| 8 | 787.652 | 821.3382 | 788.2291 | 787.652 | 787.652 | 795 | 15.00 | 58 | 7.3 | 7.609775305 |
| 9 | 1924.8644 | 1533.331 | 1727.2909 | 1718.0022 | 1855.307 | 1752 | 150.11 | 578 | 33.0 | 34.53436058 |
| 10 | 1643.6372 | 1477.7094 | 1486.3356 | 1554.3509 | 1555.0996 | 1543 | 66.85 | 257 | 16.7 | 17.45512646 |
| 11 | 1102.7736 | 1102.7736 | 1102.7736 | 1102.7736 | 1102.7736 | 1103 | 0.00 | 0 | 0.0 | 0 |
| 12 | 3911.3286 | 3911.7861 | 3911.3286 | 3911.6787 | 3911.9992 | 3912 | 0.29 | 1 | 0.0 | 0.030238054 |
| 13 | 5222.5367 | 5153.0005 | 5153.0005 | 5222.5367 | 5153.2036 | 5181 | 38.05 | 147 | 2.8 | 2.959737113 |
| 14 | 3277.0673 | 3325.3886 | 3346.5749 | 3286.2045 | 3235.0641 | 3294 | 43.50 | 168 | 5.1 | 5.322299714 |
| 16 | 36.7006 | 36.7006 | 36.7006 | 36.7006 | 36.7006 | 37 | 0.00 | 0 | 0.0 | 0 |
| 17 | 395.0539 | 395.0539 | 395.0539 | 395.0539 | 395.0539 | 395 | 0.00 | 0 | 0.0 | 5.50331E−06 |
| 18 | 5450.6448 | 5450.6448 | 5450.6448 | 5450.6448 | 5450.6448 | 5451 | 0.00 | 0 | 0.0 | 0 |
| 19 | 9187.3002 | 9199.4373 | 9187.3002 | 9187.3002 | 9187.3002 | 9190 | 5.43 | 21 | 0.2 | 0.23803035 |
| 20 | 8702.6044 | 8704.4868 | 8637.662 | 8744.231 | 8499.4516 | 8658 | 96.35 | 371 | 4.3 | 4.485094278 |
| 24 | 370.4966 | 340.469 | 345.5483 | 237.4559 | 299.3495 | 319 | 52.09 | 201 | 62.9 | 65.87340088 |
| 26 | 216.0155 | 216.0155 | 216.0155 | 267.6556 | 216.0155 | 226 | 23.09 | 89 | 39.3 | 41.11866945 |
| 27 | 393.0941 | 316.8948 | 416.9703 | 377.2603 | 443.0711 | 389 | 47.59 | 183 | 47.1 | 49.24334744 |
| 28 | 813.2213 | 782.7559 | 809.9898 | 783.0572 | 848.0357 | 807 | 26.89 | 104 | 12.8 | 13.42025606 |
| 32 | 2694.7855 | 2379.9089 | 1818.8017 | 2598.2624 | 2594.5693 | 2417 | 353.82 | 1362 | 56.4 | 58.98873746 |
| 34 | 135.7673 | 119.5965 | 135.7673 | 135.7673 | 135.7673 | 133 | 7.23 | 28 | 21.0 | 21.99009281 |
| 35 | 479.5001 | 435.0798 | 394.6555 | 394.6555 | 394.6555 | 420 | 37.73 | 145 | 34.6 | 36.22809801 |
| Somme | 62081.4075 | 60916.719 | 60764.3873 | 61412.2477 | 61558.3353 | 2453.9 | 52.5 | 202.0 | 15.5 | 16.2 |

Finally, Table 3 illustrates the improvement obtained in the prediction of the concentrations of the constituents of a petroleum product:

TABLE 3

Improvement obtained in the concentration prediction

| Concentration | C4-DI-AROMATICS | C12-N-PARAFFINS |
|---|---|---|
| Before tightening | 9.3% m/m | 0.42% m/m |
| After tightening | 11% m/m | 0.36% m/m |

Advantages

The automatic tightening of each polygon is based on physical criteria: each column of the image corresponds to a two-dimensional gas chromatography signal from the second column. The lower (respectively upper) boundary of a polygon thus has to correspond to a start (respectively an end) of an elution peak on the 1D signal.

These processings allow on the one hand minimizing the processing time (via application of the mask and automatic tightening) and on the other hand improving the repeatability and the accuracy (via automatic tightening).

The method according to the invention can thus be applied to the determination of the mass composition of hydrocarbons and other constituents of products from the chemical or petroleum industry. It allows improving the accuracy and the repeatability of the analyses.

Tableaux 1 et 2
Blob numéro: blob number
Moyenne: average
Ecart-type: standard deviation
Intervalle de confiance à 99%: 99% confidence interval
Ecart relatif: relative deviation
Erreur de dispersion: dispersion error
Somme: sum.

The invention claimed is:

1. A method for quantitative analysis of a mixture of molecular compounds by two-dimensional gas chromatography using a two-dimensional gas chromatography device, wherein a chromatogram in two dimensions is generated from a chromatographic signal provided by a detector and chromatographic peaks are selected by means of polygons, comprising for at least one polygon:
   (a) adjusting with a processor each polygon by identifying portions of the chromatographic signal contained in each polygon
   determining start times, end times and maximums for chromatographic peaks present in the portions; and
   adjusting each polygon with a processor by shifting intersection points between each polygon and the portions, according to the start times, the end times and the maximums of the chromatographic peaks; and
   (b) determining an amount of at least one molecular compound by calculating the surface area of the adjusted at least one polygon.

2. A method as claimed in claim 1, wherein each polygon is adjusted for each intersection point comprising:
   if the intersection point is contained between starting and the maximum of a chromatographic peak, the intersection point is shifted towards a peak start point and if the intersection point is contained between the maximum and the end of a chromatographic peak, the point is shifted towards a peak end time; and
   if the intersection point is not contained between a start time and an end time of a chromatographic peak, the intersection point is shifted vertically along a signal portion towards a closest peak, as long as the intersection point does not merge with a boundary of the polygon, with a boundary of the chromatogram, or with a starting or ending chromatographic peak.

3. A method as claimed in claim 2, wherein each polygon is adjusted starting from a first intersection point and as long as a last point is not processed, by removing a point from a middle if a current point is aligned with a next two points, and goes two points back, or goes to a next point.

4. A method as claimed in claim 3, wherein each polygon is adjusted by calculating a final position of a vertex of each polygon by linear interpolation with respect to neighboring vertices.

5. A method as claimed in claim 4 wherein spots are defined by manual construction of each polygon.

6. A method as claimed in claim 5, wherein chromatographic peaks are selected by a polygon mask for use with two-dimensional gas chromatography, by replacing each vertex forming each polygon on a closest portion of the signal.

7. A method as claimed in claim 4, wherein chromatographic peaks are selected by a polygon mask for use with two-dimensional gas chromatography, by replacing each vertex forming each polygon on a closest portion of the signal.

8. A method as claimed in claim 3 wherein spots are defined by manual construction of each polygon.

9. A method as claimed in claim 8, wherein chromatographic peaks are selected by a polygon mask for use with two-dimensional gas chromatography, by replacing each vertex forming each polygon on a closest portion of the signal.

10. A method as claimed in claim 3, wherein chromatographic peaks are selected by a polygon mask for use with two-dimensional gas chromatography, by replacing each vertex forming each polygon on a closest portion of the signal.

11. A method as claimed in claim 2, wherein each polygon is adjusted by calculating a final position of a vertex of each polygon by linear interpolation with respect to neighboring vertices.

12. A method as claimed in claim 11 wherein spots are defined by manual construction of each polygon.

13. A method as claimed in claim 12, wherein chromatographic peaks are selected by a polygon mask for use with two-dimensional gas chromatography, by replacing each vertex forming each polygon on a closest portion of the signal.

14. A method as claimed in claim 11, wherein chromatographic peaks are selected by a polygon mask for use with two-dimensional gas chromatography, by replacing each vertex forming each polygon on a closest portion of the signal.

15. A method as claimed in claim 2, wherein spots are defined by manual construction of each polygon.

16. A method as claimed in claim 15, wherein chromatographic peaks are selected by a polygon mask for use with two-dimensional gas chromatography, by replacing each vertex forming each polygon on a closest portion of the signal.

17. A method as claimed in claim 2, wherein chromatographic peaks are selected by a polygon mask for use with two-dimensional gas chromatography, by replacing each vertex forming each polygon on a closest portion of the signal.

18. A method as claimed in claim 2, wherein the start times, the end times and maximums of chromatographic peaks are determined from first, second and third derivatives of the portions of the chromatographic signal.

19. A method as claimed in claim 18, wherein the derivatives are calculated by Savitzky-Golay filtering.

20. A method as claimed in claim 1, wherein each polygon is adjusted starting from a first intersection point and as long as a last point is not processed, by removing a point from a middle if a current point is aligned with a next two points, and goes two points back, or goes to a next point.

21. A method as claimed in claim 20, wherein each polygon is adjusted by calculating a final position of a vertex of each polygon by linear interpolation with respect to neighboring vertices.

22. A method as claimed in claim 21 wherein spots are defined by manual construction of each polygon.

23. A method as claimed in claim 22, wherein chromatographic peaks are selected by a polygon mask for use with two-dimensional gas chromatography, by replacing each vertex forming each polygon on a closest portion of the signal.

24. A method as claimed in claim 21, wherein chromatographic peaks are selected by a polygon mask for use with two-dimensional gas chromatography, by replacing each vertex forming each polygon on a closest portion of the signal.

25. A method as claimed in claim 20 wherein spots are defined by manual construction of each polygon.

26. A method as claimed in claim 20, wherein chromatographic peaks are selected by a polygon mask for use with two-dimensional gas chromatography, by replacing each vertex forming each polygon on a closest portion of the signal.

27. A method as claimed in claim 1, wherein each polygon is adjusted by calculating a final position of a vertex of each polygon by linear interpolation with respect to neighboring vertices.

28. A method as claimed in claim 27 wherein spots are defined by manual construction of each polygon.

29. A method as claimed in claim 28, wherein chromatographic peaks are selected by a polygon mask for use with two-dimensional gas chromatography, by replacing each vertex forming each polygon on a closest portion of the signal.

30. A method as claimed in claim 27, wherein chromatographic peaks are selected by a polygon mask for use with two-dimensional gas chromatography, by replacing each vertex forming each polygon on a closest portion of the signal.

31. A method as claimed in claim 1, wherein spots are defined by manual construction of each polygon.

32. A method as claimed in claim 31, wherein chromatographic peaks are selected by a polygon mask for use with two-dimensional gas chromatography, by replacing each vertex forming each polygon on a closest portion of the signal.

33. A method as claimed in claim 1, wherein chromatographic peaks are selected by a polygon mask for use with two-dimensional gas chromatography, by replacing each vertex forming each polygon on a closest portion of the signal.

34. A method as claimed in claim 25, wherein chromatographic peaks are selected by a polygon mask for use with two-dimensional gas chromatography, by replacing each vertex forming each polygon on a closest portion of the signal.

35. A method as claimed in claim 1, wherein the start times, the end times and maximums of chromatographic peaks are determined from first, second and third derivatives of the portions of the chromatographic signal.

* * * * *